(12) United States Patent
Engelaar et al.

(10) Patent No.: US 9,452,943 B2
(45) Date of Patent: Sep. 27, 2016

(54) ANAEROBIC WATER PURIFICATION SYSTEM AND METHOD FOR TREATING A LIQUID

(71) Applicant: Aqana B.V., CJ Leeuwarden (NL)

(72) Inventors: Antonius Johannes Hendrikus Hyacinthus Engelaar, CJ Leeuwarden (NL); Sanne Steenbrink, CJ Leeuwarden (NL); Alje Haan, CJ Leeuwarden (NL)

(73) Assignee: Aqana B.V., Sneek (NL)

( * ) Notice: Subject to any disclaimer, the term of this patent is extended or adjusted under 35 U.S.C. 154(b) by 137 days.

(21) Appl. No.: 14/374,895

(22) PCT Filed: Feb. 7, 2013

(86) PCT No.: PCT/NL2013/050074
§ 371 (c)(1),
(2) Date: Jul. 25, 2014

(87) PCT Pub. No.: WO2013/119119
PCT Pub. Date: Aug. 15, 2013

(65) Prior Publication Data
US 2014/0367329 A1    Dec. 18, 2014

(30) Foreign Application Priority Data

Feb. 9, 2012 (NL) ..................... 2008266

(51) Int. Cl.
*C02F 3/28* (2006.01)
*C02F 11/04* (2006.01)
(Continued)

(52) U.S. Cl.
CPC ........... *C02F 3/2853* (2013.01); *C02F 3/2806* (2013.01); *C02F 3/2833* (2013.01);
(Continued)

(58) Field of Classification Search
CPC .. C02F 3/2853; C02F 3/2806; C02F 3/2833; C02F 3/2893; C02F 11/04; C02F 2103/28; C02F 2103/32; C02F 2209/03; C02F 2203/00; C12M 21/04; C12M 23/36; C12M 41/40; Y02E 50/343

USPC ........... 210/603, 614, 615, 616, 617, DIG. 9
See application file for complete search history.

(56) References Cited

U.S. PATENT DOCUMENTS 2,202,772 A * 5/1940 Durdin, Jr. ................ C02F 3/02
                                                              210/187
4,256,573 A    3/1981 Shimodaira et al.
(Continued)

FOREIGN PATENT DOCUMENTS

AT        195459 B      2/1958
CH        657150 A5     8/1986
(Continued)

OTHER PUBLICATIONS

Appels et al. "Principles and potential of the anaerobic digestion of waste-activated sludge", Progress in Energy and Combustion Science, vol. 34, No. 6, Dec. 1, 2008, pp. 755-781.

*Primary Examiner* — Fred Prince
(74) *Attorney, Agent, or Firm* — Bret E. Field; Bozicevic, Field & Francis LLP

(57) ABSTRACT

The invention relates to an anaerobic water purification system, conversion kit and method for treating a liquid. The anaerobic water purification system according to the invention comprises: —a container for the liquid for treatment provided during use with a sludge bed; —a supply conduit operatively connected to the container for supplying the liquid for treatment; —a distribution system connected to the supply conduit for distributing the liquid over the sludge bed from above; —carrier material which is arranged during use in the container and to which anaerobic sludge material can attach; and—a gas roof arranged at or on the container and provided with a volume which can be adapted during use to the biogas production. The carrier material is preferably free-floating material. The discharge conduit for discharge of treated liquid is preferably connected to a riser pipe.

20 Claims, 3 Drawing Sheets

(51) Int. Cl.
*C12M 1/107* (2006.01)
*C12M 1/34* (2006.01)
*C02F 103/28* (2006.01)
*C02F 103/32* (2006.01)

(52) U.S. Cl.
CPC .............. *C02F 3/2893* (2013.01); *C02F 11/04* (2013.01); *C12M 21/04* (2013.01); *C12M 23/36* (2013.01); *C12M 41/40* (2013.01); *C02F 2103/28* (2013.01); *C02F 2103/32* (2013.01); *C02F 2203/00* (2013.01); *C02F 2209/03* (2013.01); *Y02E 50/343* (2013.01)

(56) References Cited

U.S. PATENT DOCUMENTS

| | | | | |
|---|---|---|---|---|
| 4,311,593 A | * | 1/1982 | Benjes | C02F 3/2806 210/603 |
| 4,676,906 A | * | 6/1987 | Crawford | C02F 1/006 210/603 |
| 5,185,079 A | | 2/1993 | Dague | |
| 5,228,995 A | * | 7/1993 | Stover | C02F 1/006 210/150 |
| 5,747,311 A | | 5/1998 | Jewell | |
| 6,451,206 B1 | * | 9/2002 | Charbonneau | C12M 21/04 210/170.09 |
| 2002/0079266 A1 | * | 6/2002 | Ainsworth | C02F 3/28 210/603 |
| 2009/0050560 A1 | | 2/2009 | Dos Santos Alves et al. | |

FOREIGN PATENT DOCUMENTS

| | | |
|---|---|---|
| DE | 102007025807 A1 | 12/2008 |
| DE | 102011106757 A1 | 1/2012 |
| EP | 1354940 A2 | 10/2003 |
| EP | 1818315 A1 | 8/2007 |
| EP | 2394966 A1 | 12/2011 |
| WO | 02/096806 A2 | 12/2002 |

* cited by examiner

ANAEROBIC WATER PURIFICATION SYSTEM AND METHOD FOR TREATING A LIQUID

The present invention relates to an anaerobic water purification system for treating a liquid. Such a liquid is particularly a wastewater flow from for instance the process industry.

Diverse water purification systems are known in practice. These include so-called aerobic and anaerobic water purification systems. Both involve a biological purification in which use is made of micro-organisms to degrade organic material.

A problem with aerobic systems is the relatively low conversion and the creation of a large amount of sludge that has to be disposed of and possibly processed. In addition, a relatively large amount of energy is required for, among other purposes, aerators for providing aerobic conditions during the purification.

Anaerobic systems have the advantage that no oxygen need be supplied and that the system can therefore usually be embodied in simple and more energy-efficient manner. In anaerobic systems the organic material is degraded in a number of steps to eventually form $CO_2$ and methane, i.e. biogas. In conventional anaerobic wastewater purification systems the flow for purifying is carried through a layer in which the micro-organisms are present in order to thereby bring about the conversion/purification.

Conventional anaerobic systems make use for this purpose of three-phase separators or settlers. These three-phase separators are used for the purpose of separating the sludge, gas and water flows. This requires additional components in the system, whereby such systems involve considerable additional investment.

The present invention has for its object to provide an improved anaerobic water purification system with which the purification can be carried out in more effective manner.

The present invention provides for this purpose an anaerobic water purification system for treating a liquid according to the invention, the system comprising:
- a container for the liquid for treatment provided during use with a sludge bed;
- a supply conduit operatively connected to the container for supplying the liquid for treatment;
- a distribution system connected to the supply conduit for distributing the liquid over the sludge bed from above;
- carrier material which is arranged during use in the container and to which anaerobic sludge material can attach; and
- a gas roof arranged at or on the container and provided with a volume which can be adapted during use to the biogas production.

A container comprises for instance a storage vessel or tank into which the liquid for treatment can be introduced. The liquid is particularly a wastewater flow, for instance from the process industry, such as the paper industry, beer industry and so on. The liquid may however also comprise other flows. Other components may possibly be present in the liquid in dissolved and/or solid form. The liquid is supplied via a supply conduit and subsequently distributed over substantially the whole surface of the container. According to the invention the liquid is introduced here from above, after which the liquid for purifying, for instance wastewater, flows downward in the container. By arranging carrier material to which anaerobic sludge material can attach in the container the flow for treatment comes into contact with the anaerobic micro-organisms present therein.

The preferred carrier material relates to free-floating carriers. A type of fluid bed reactor is hereby obtained. It has been found that a good mixing and associated conversion is hereby realized compared to conventional anaerobic systems. A further description of preferred embodiments of such carriers is given in WO 02/096806, the content of which should be deemed as included herein. Provided in particular here is the specific description of the carrier material, with attachment of the aerobic material thereto, in addition to a suitable configuration, for instance cylindrical with radially extending surfaces. It has been found that this type of carrier material is highly suitable for attachment of anaerobic sludge material thereto.

According to the invention use is preferably made of carriers with a density of about 0.8-0.99 times the density of water such that the carriers float of their own accord. The preferably employed specific surface is less than 2000, preferably less than 1500 and most preferably between 600-700 $m^2/m^3$.

In an embodiment the water purification system according to the invention can further be operated in continuous manner. An effective purification is hereby realized.

The system according to the invention preferably functions as an anaerobic water purification system, and therefore not as for instance a conventional fermenter of biomass, such as a sludge fermenter in sewage treatment.

Introducing the flow for treatment into the container from above and then guiding it through the carrier material with the sludge material thereon achieves the desired purification. An effective purification is hereby realized.

The combination of a container and carrier material preferably arranged free-floating therein, wherein the distribution system introduces the liquid for treatment from above, provides a so-called downward flow or downflow system. This means that no forced settling with settlers is necessary, since the sludge material floats through the carrier material. An effective and better manageable system is hereby obtained which has been found particularly suitable for conversion of already existing containers used for instance for conventional aerobic systems.

In addition, the fluid bed of carriers and the introduction of liquid from above realize a downward flow. The produced biogas will move upward. A settler or three-phase separator is hereby not required, so that a cost-efficient embodiment of the anaerobic system is realized. It has additionally been found that the effectiveness of the conversion is further improved, and more readily controllable, by applying a back-flow in the container, so that the process can be performed in more efficient manner.

The anaerobic conversion produces a biogas, in particular methane, and carbon dioxide. By providing a gas roof, particularly a gas roof with a volume which can be adapted to the production of the biogas, a desired pressure can be maintained within a desired range in the container. Because the produced biogas will move upward, it flows counter to the effluent for treatment, thereby bringing about an improved mixing.

The gas roof is preferably arranged such that a pressure buildup is hereby made possible during use. This makes it possible for instance to "push" water out of the system, resulting in an effective, anaerobic water purification system. It has been found that an overpressure of about 0-1 bar, for instance about 10-200 mbar, and preferably about 30-50 mbar is effective here. An additional advantage hereof is that more $CO_2$ is dissolved in the liquid due to the higher pressure. Precipitation, in particular the deposition of calcium (limescale) on carrier material, is hereby reduced such that less purification and/or cleaning is necessary. A further additional advantage is that the quality of the produced biogas is increased due to the lower concentration of $CO_2$ therein, such that further treatment steps can be performed more efficiently.

The volume beneath the gas roof is preferably adjustable during use by using a flexible material. The volume is preferably adjusted autonomously here as a result of the pressure buildup in the volume. In this currently preferred embodiment the volume is therefore adjusted autonomously during use to the actually produced biogas production using a flexible roof instead of an off-line fixed specification of the volume during the design of the system.

The gas roof is preferably arranged with connecting means on an existing container. It is possible in this way to provide an already existing container or tank with a gas roof and to then use this container as anaerobic water purification system. The liquid for treatment is here purified, resulting in a pure, or at least purer, water flow and further flows, including sludge and biogas.

The gas roof preferably consists of a gas membrane which is as it were inflated by the produced biogas. In the currently preferred embodiment this biogas membrane is provided inside a covering roof material which is held in position using for instance an air blower. Such an air blower blows air between the covering roof and the gas membrane. When the anaerobic water purification system according to the invention is out of operation, the biogas membrane will not need to provide any volume for the produced biogas and will therefore for instance rest on a grating preferably placed just above the distributors. Alternatively, it is also possible to provide a fixed covering roof, for instance in the form of a gable roof. Use is preferably also made here of a flexible gas membrane situated under this outer roof and providing a flexible volume in the same manner.

The connecting means preferably comprise clamping mechanisms, wherein the gas membrane is clamped at or on the container. This clamping connection is preferably provided in substantially wholly gas-tight manner under the usual process conditions so that the biogas cannot escape in uncontrolled manner from the flexible biogas volume of the system according to the invention.

In a currently preferred embodiment the gas roof is provided over a part of an existing container, and another part of the existing container is provided during use as pretreatment and/or post-treatment container. An existing container relates in particular to a conventional aerobic water purification with the system according to the invention which is made suitable for an anaerobic water purification system. It has been found that the anaerobic system here only requires a part of the volume of the previously aerobic container. It is hereby possible to utilize a significant part of the existing container, i.e. $2/3$ to $4/5$ of the volume, for a pretreatment and/or post-treatment. The other part is then utilized for the anaerobic treatment of the liquid.

It is also possible to provide a sub-container in the container of a conventional aerobic system. An additional safety buffer is hereby provided, whereby the process can be performed still more safely.

The utilization of preferably a part of the volume of the formerly aerobic container for an anaerobic system, about 20 to 25% being found particularly advantageous in most cases, makes it possible to achieve the same treatment capacity as in for instance a previously used aerobic system. This is particularly advantageous when a greater capacity is required. At such a moment a somewhat larger volume than this 20 to 25%, for instance 25 to 90%, can be utilized for an anaerobic system, and the remainder of the volume of the formerly for instance aerobic container can be utilized for pretreatment and/or post-treatment. It has been found that this is particularly advantageous in situations where an alternative approach would require an additional or an extended aerobic system. An improved purification with increased capacity can hereby be achieved with limited investment, whereby the total process performance is improved in respect of process-oriented aspects and from a cost viewpoint.

In an advantageous preferred embodiment according to the present invention the distribution system comprises a feed, a number of distributors and a flushing connection.

By making use of a number of distributors the liquid for treatment can be distributed over substantially the whole upper surface of the liquid in the container. This achieves that a good distribution is realized and a good flow through the anaerobic sludge bed is achieved. A conversion of the organic material in water and residual material to the biogas is hereby improved. Providing a flushing connection makes it possible to clean the feed system with the distributors in effective manner. This prevents blockages and other problems and guarantees a good operation.

Distribution tanks are preferably provided in flow direction of the supplied liquid upstream and/or downstream of the distributors. Such distribution or buffer tanks, or headers, form a type of central supply buffer for distributing the flow over the distributors. A good distribution over all distributors is effected by placing them upstream of the distributors. An improved cleaning of the supply system can be realized by preferably placing an additional (collection) tank downstream of the distributors. Use is for instance made here of an additional cleaning connection. This cleaning is for instance performed with water, optionally provided with a number of additives. Use is made here of flushing and/or back-flushing of the conduits.

In an advantageous preferred embodiment according to the present invention the system comprises a discharge system for treated liquid arranged in or close to the bottom of the container.

The downward flow, i.e. the downflow character of the system, is realized by providing a discharge system at the bottom. Such a discharge system can for instance comprise a central opening or vessel from which a discharge conduit discharges the effluent. A plurality of discharge points, for instance in the form of an opening in a vessel, can also be provided if desired, optionally each with individual discharge conduits. Possible undesired preferred flows can be influenced and preferably prevented by the discharge system.

In an alternative preferred embodiment the discharge system comprises piping, for instance a hose, preferably a flexible hose, which is provided with a number of openings. The advantage hereof is that such piping, for instance a flexible hose, can as it were be laid on the bottom of a container, particularly an already existing container, for instance one formerly used as a conventional aerobic system. This achieves that there is the possibility of discharge over substantially the whole bottom surface. Blockage of openings is also prevented, since discharge of effluent is possible through a plurality of openings. An additional advantage is that, in the case of a conversion from an aerobic to an anaerobic system according to the invention, such a discharge system can be realized in relatively simple manner by placing such piping on the bottom of a container.

In a further advantageous preferred embodiment according to the present invention the discharge system comprises a riser pipe.

Providing a riser pipe in the discharge system achieves that a guaranteed liquid level is present in the container when the system is in use. The system does not hereby depend on a single shut-off valve which, if it fails, results in an uncontrolled level in the container and/or draining of the container. The discharged effluent is once again carried up to a specific height by the riser pipe, after which the effluent is discharged further. This effluent is pressed upward in the riser pipe by the pressure of the liquid column in the container. This pressure is increased in the container by the pressure caused by the biogas. This means in practice that the liquid level in the riser pipe will be slightly higher than the liquid level in the container. A safe system is hereby provided.

The riser pipe preferably comprises a height-adjustable drain. Providing a height-adjustable drain makes it possible to vary the liquid level in the container within a range in effective manner. It is possible here to set the drain such that the pressure in the biogas compartment is controlled. If the biogas pressure rises too high, it will press the liquid level in the container further downward, whereby more liquid is discharged. The safety of the system is hereby increased further.

The produced biogas is preferably used to generate energy. This generated energy is more preferably used to drive the pumps required in the system, whereby an energetically self-sufficient purification system is obtained. It is hereby possible for instance to place such a system at any desired location, since there is no great dependence on a fixed electricity supply. Use can optionally be made of a generator to start up the process.

A pressure-reducing valve is preferably arranged in a gas outlet of the volume under the gas roof. In a currently preferred embodiment the valve is provided between the volume under the gas roof and a gas buffer. The pressure is for instance reduced from 1 bar to 30 mbar of overpressure. The connection is squeezed for this purpose by applying a pressure to the outer side of the connection. This pressure is for instance realized with a gas pressure from a preferably inert gas so as to avoid risks with a flammable mixture in the case of possible leakage in the connection.

In a further advantageous preferred embodiment the system comprises a gas distribution system for produced biogas and/or external gas, for instance the inert $N_2$, which can be introduced into the container from the underside.

Use of the gas distribution system makes it possible to realize a continuous or periodic additional mixing of the carrier material with the sludge material thereon. This for instance avoids the possibility of "dead spaces" and/or preferred flows occurring in the container. This further increases the overall effectiveness of the purifying process. Introduction of the gas from below further effects a backflow with the liquid, whereby mixing is further improved. The introduction of the gas serves substantially to prevent formation of channels. This introduction need therefore usually only be carried out periodically.

The invention also relates to a conversion kit for converting an existing container to an anaerobic water purification system as described above, wherein the kit comprises a gas roof for at least a part of the existing container, connecting means for connecting the gas roof to the container, supply and discharge means for the liquid for treatment and the treated liquid and the biogas, and carrier material, preferably placed in free-floating manner, to which sludge material can attach.

Such a conversion kit provides the same effects and advantages as described above for the anaerobic water purification system. It has been found that the kit according to the invention can be used in effective manner to convert conventional aerobic systems to an anaerobic system according to the invention. Such a container is provided for this purpose with a gas roof, preferably with a flexible gas membrane, by making use of connecting means comprising for instance a clamping mechanism. Supply conduits and discharge conduits serve here to realize the required flows of the liquid for treatment and discharge of the effluent. In addition, use is made of preferably freely placed carrier material to which biomass can attach.

The invention further also relates to a method for anaerobic treatment of liquid, the method comprising of:

arranging a gas roof on a container and a discharge for the biogas;

providing on or in the container:

at least one supply conduit and a distribution system for distributing the liquid over the container from above;

a quantity of carrier material; and a discharge conduit for guiding treated liquid out of the container from below, wherein the discharge conduit is operatively connected to a riser pipe for keeping the container filled during use.

Such a method for treating, and particularly purifying, a liquid, in particular a wastewater flow, provides the same effects and advantages as described above for the anaerobic water purification system and the conversion kit. The produced biogas is preferably used to generate energy and thereby provide a self-sufficient system in which the generated energy is used for the purpose of performing the process.

Further advantages, features and details of the invention are elucidated on the basis of preferred embodiments thereof, wherein reference is made to the accompanying drawings, in which.

Figure 1:
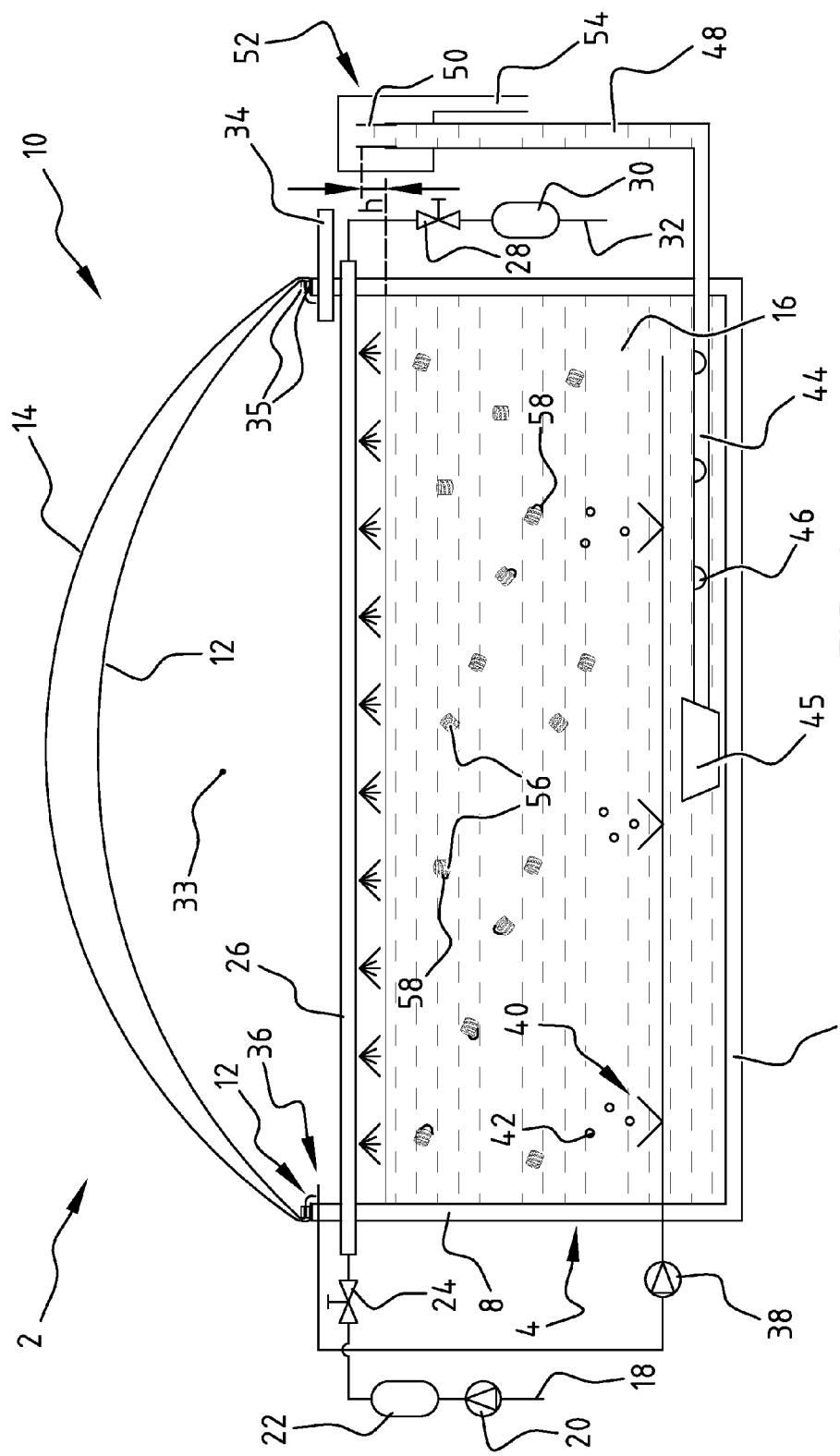
FIG. 1 shows an overview of the system according to the invention.

An anaerobic water purification system 2 (FIG. 1) is provided with a container 4 consisting of a bottom 6 and wall parts 8. Container 4 is further provided with a roof 10 consisting of a gas membrane 12 and an outer roof 14. In a rest position membrane 12 is located on a grating (not shown) above the liquid 16 in container 4. The wastewater flow for treatment is fed via feed 18, pump 20, buffer or header 22 and a shut-off valve 24 to the distributors 26 above the liquid 16 in container 4. In the shown embodiment a shut-off valve 28, buffer or header 30 and connection 32 are also provided for the purpose of flushing the distribution system and/or flushing and/or blowing it clean. Produced biogas is discharged via discharge 34 and optionally further used to generate energy. Via circulation conduit 36 produced biogas is transported via pump 38 to openings or nozzles 40, whereby gas bubbles 42 can be introduced into liquid 16.

In the shown embodiment a discharge conduit 44 is arranged coupled to vessel 45 on bottom 6 and optionally provided with a number of openings 46 for carrying effluent out of container 4. This effluent is guided via riser pipe 48, in which a flexible drain or overflow 50 is provided in the shown embodiment, via reservoir 52 to discharge 54. The height difference h is adjustable via drain or overflow 50, wherein the height difference relates to the height of the liquid level in riser pipe 48 and the height of the liquid 16 in container 4. This height difference is designated with h, which is a measure of the pressure of the produced biogas in biogas compartment 33.

The gas membrane is fixed on a wall part 8 using a clamping mechanism 35, wherein in the shown embodiment gas membrane 12 is arranged on the inner side of container 4. Outer part 14 is preferably tensioned by making use of an air blower which blows air into the intermediate space between outer part 14 and membrane 12 (not shown). Present in liquid 16 is a carrier material 56 of a preferably plastic material of a maximum size of preferably several centimeters, or even smaller, on which sludge material 58 can be present. Carriers 56 are described in more detail in WO 02/096806.

Figure 2:
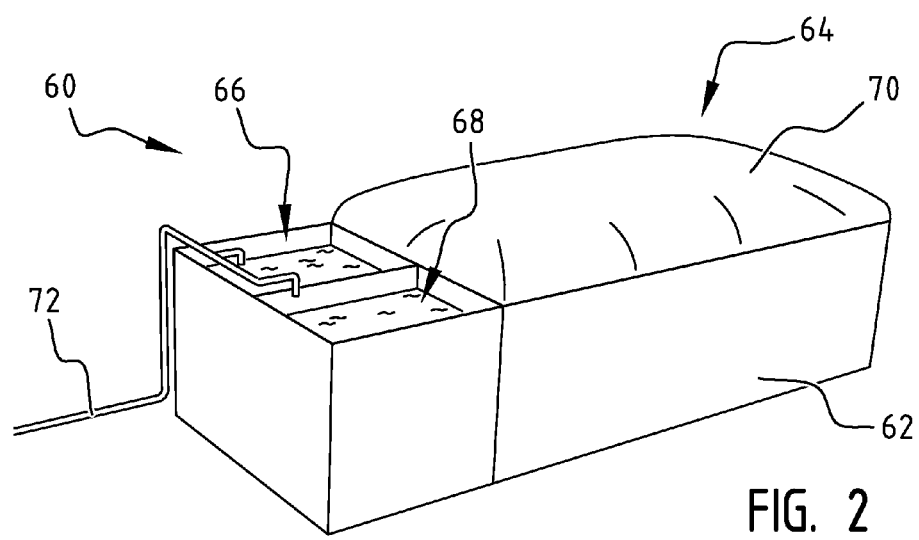
FIG. 2 shows a view of a system of FIG. 1 and conversion.

An anaerobic water purification system 60 (FIG. 2) comprises a container or tank 62, for instance of a conventional aerobic system which is being converted. A part of the volume of tank 62 is utilized for this purpose as anaerobic system 64, wherein further parts 66, 68 are used in the shown embodiment for pretreatment or post-treatment of the process flows. Anaerobic system 64 is provided with gas roof 70. System 60 is further provided with a number of conduits 72.

Figure 3:
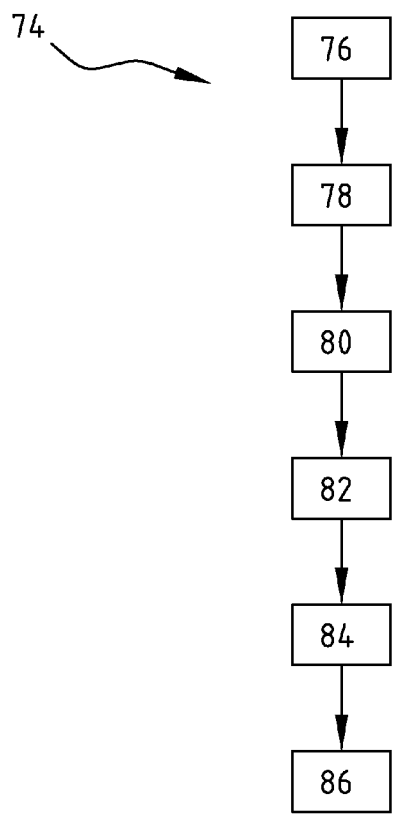
FIG. 3 shows a schematic representation of the conversion of a conventional system to the system according to the invention.

A conversion process 74 (FIG. 3) from a previously conventional aerobic system 76 requires in a first dimensioning step 78 that the required volumes and materials are defined. In a subsequent method step 80 a roof, preferably a gas membrane, is also provided on the conventional container, and in further step 82 supply and discharge conduits are arranged as well as optional circulation conduits. Optional throughfeeds are arranged here in wall 8 of container 4. It has been found here that it is possible to suffice with a limited number of throughfeeds, whereby the conversion of a conventional system to system 2, 60 according to the invention can be carried out in relatively simple manner. In the final preparatory step 84 carrier material 56 is then added to container 4, followed by setting into operation 86, wherein the various settings of the process are further determined.

Figure 4:
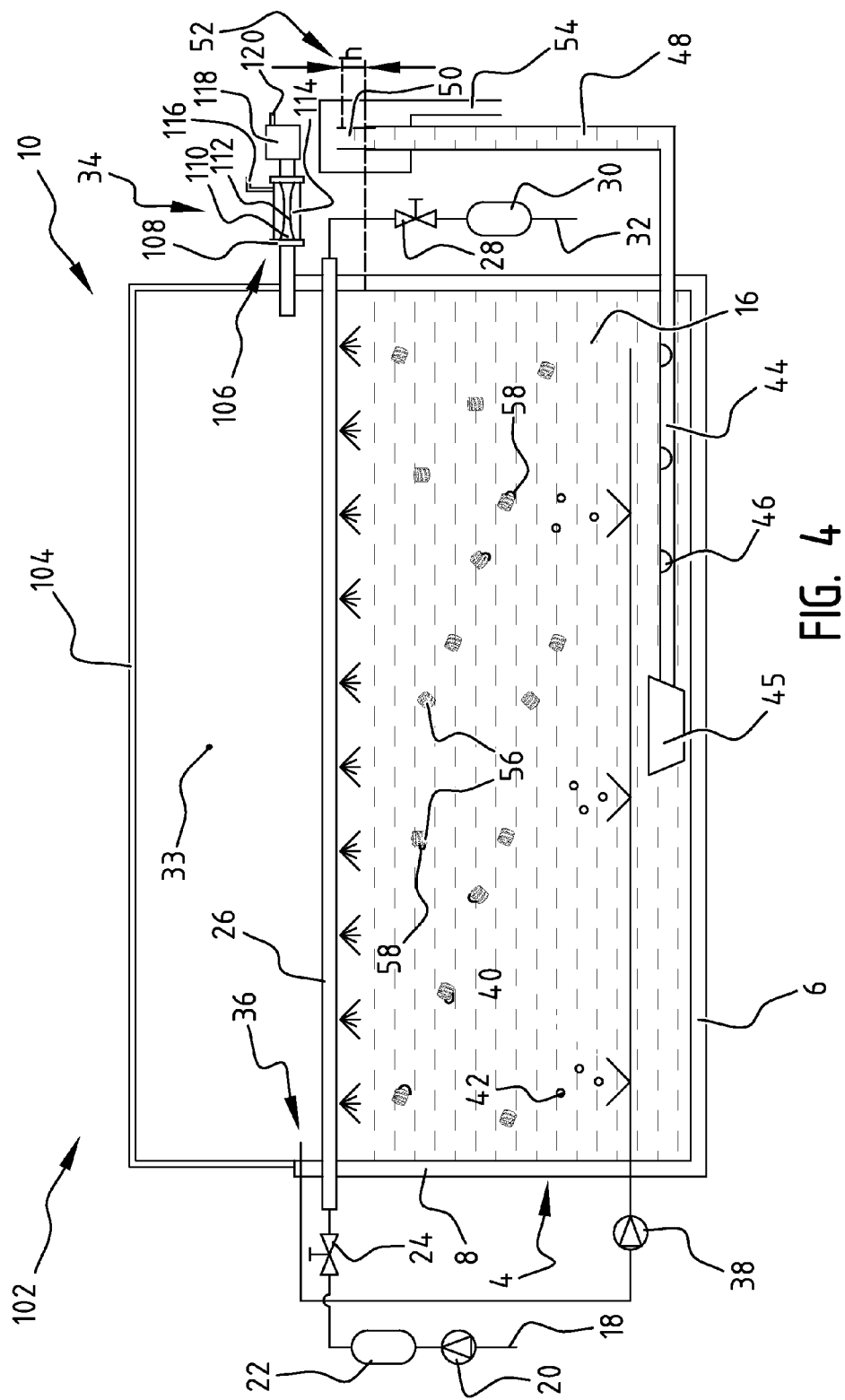
FIG. 4 shows an alternative embodiment of the system according to the invention.

In an alternative embodiment, system 102 (FIG. 4) is provided with a fixed roof 104. Components which can be provided in similar manner as in other embodiments discussed above are shown for the greater part with the same reference numerals. In addition to fixed roof 104, system 102 is provided with a pressure-reducing valve 106 in gas outlet 34. Valve 106 with flanges 108 is provided in discharge 34. Valve 106 has a passage 110 which is adjustable using adjustable casing 112. Casing 112 is pressed inward by the pressure in space 114 which is set with gas inlet 116. Outlet 34 is further provided with gas buffer 118 with outlet 120.

It will be apparent to the skilled person that diverse components of the shown embodiments are optional and/or can be embodied in other similar ways. It is also possible to use components, for instance valve 106, in other embodiments.

The present invention is by no means limited to the above described embodiments thereof. The rights sought are defined by the following claims, within the scope of which many modifications can be envisaged.

The invention claimed is:

1. An anaerobic water purification system for treating a liquid, comprising:
   a container for the liquid for treatment provided during use with a sludge bed;
   a supply conduit operatively connected to the container for supplying the liquid for treatment;
   a distribution system connected to the supply conduit for distributing the liquid over the sludge bed, wherein the distribution system distributes the liquid from above over substantially an entire upper surface of the liquid in the container, thereby providing a downward flow of the liquid in the container;
   carrier material which is arranged during use in the container and to which anaerobic sludge material can attach; and
   a gas roof arranged at or on the container and comprising a flexible material, wherein the gas roof is provided with a volume which can be adapted during use, by using the flexible material, to biogas production from degrading organic material.

2. The anaerobic water purification system as claimed in claim 1, wherein the gas roof enables a pressure buildup during use.

3. The anaerobic water purification system as claimed in claim 2, wherein the volume is autonomously adjustable during use.

4. The anaerobic water purification system as claimed in claim 1, wherein the gas roof can be arranged with connecting means on an existing container.

5. The anaerobic water purification system as claimed in claim 4, wherein the gas roof is provided over a part of the existing container, and another part of the existing container is provided during use as pretreatment and/or post-treatment container.

6. The anaerobic water purification system as claimed in claim 1, wherein the distribution system comprises a feed, a number of distributors and a flushing connection.

7. The anaerobic water purification system as claimed in claim 1, wherein a distribution or collection tank is provided upstream and/or downstream of the distributors as seen in flow direction of the liquid.

8. The anaerobic water purification system as claimed in claim 1, further comprising a discharge system for treated liquid arranged in or close to the bottom of the container.

9. The anaerobic water purification system as claimed in claim 8, wherein the discharge system comprises a hose provided with a number of openings.

10. The anaerobic water purification system as claimed in claim 8, wherein the discharge system comprises a riser pipe.

11. The anaerobic water purification system as claimed in claim 10, wherein the riser pipe comprises a height-adjustable drain.

12. The anaerobic water purification system as claimed in claim 1, wherein the produced biogas is used to generate energy.

13. The anaerobic water purification system as claimed in claim 1, further comprising a pressure-reducing valve arranged in a gas outlet of the volume under the gas roof.

14. The anaerobic water purification system as claimed in claim 1, further comprising a gas distribution system wherein gas can be introduced into the container from the underside.

15. A conversion kit for converting an existing container to an anaerobic water purification system as claimed in claim 1, the kit comprising:
   a gas roof for at least a part of the existing container, wherein the gas roof comprises a flexible material;

connecting means for connecting the gas roof to the container;

supply and discharge means for the liquid for treatment and the treated liquid and the biogas; and carrier material which can be arranged in the container and to which sludge material can attach.

16. The anaerobic water purification system as claimed in claim 1, wherein the carrier material is free-floating.

17. A method for anaerobic treatment of liquid in a container, the method comprising:

arranging a gas roof on a container and a discharge for the biogas, wherein the gas roof comprises a flexible material configured to provide an adjustable volume under the gas roof;

providing on or in the container:

at least one supply conduit and a distribution system for distributing the liquid from above over a sludge bed provided in the container, over substantially an entire upper surface of the liquid in the container;

a quantity of carrier material; and a discharge conduit for guiding treated liquid out of the container from below, wherein the discharge conduit is operatively connected to a riser pipe for keeping the container filled during use; and adapting the volume to the production of biogas.

18. The method as claimed in claim 17, further comprising of generating energy from produced biogas.

19. The method as claimed in claim 18, further comprising of using the generated energy to perform the treatment of the liquid such that an energetically self-sufficient system is obtained.

20. The method as claimed in claim 17, wherein the carrier material is free-floating.

* * * * *